United States Patent

Acosta Mira

[11] 4,103,019
[45] Jul. 25, 1978

[54] TRITERPENE DERIVATIVES

[75] Inventor: Jose E. Acosta Mira, Madrid, Spain

[73] Assignee: Laboratorios Landerlan, S. A., Madrid, Spain

[21] Appl. No.: 620,417

[22] Filed: Oct. 7, 1975

[51] Int. Cl.$^2$ .................. C07D 207/08; A61K 31/40
[52] U.S. Cl. ............................. 424/274; 260/326.33
[58] Field of Search .................................. 260/326.33

[56] References Cited

U.S. PATENT DOCUMENTS 3,869,458  3/1975  Turner et al. ................. 260/268 PC

FOREIGN PATENT DOCUMENTS 894,265    4/1962   United Kingdom .......... 260/268 PC
1,255,098  11/1971  United Kingdom .......... 260/268 PC

OTHER PUBLICATIONS

Biorex Lab.; Chem. Abstr., vol. 57, col. 3572d (1962).
Adanin et al., Chem. Abstr., vol. 68, col. 22087q (1967).
Capra; Chem. Abstr., vol. 69, col. 1648d (1967).
Morrison et al; Organic Chemistry, p. 741 (1969).
Brain et al; J. Chem. Soc., pp. 633–636 (1961).
Doyle et al, J. Chem. Soc., pp. 578–579 (1964).
Chem. Eng. News., vol. 38, pp. 50–51 (1960).

Primary Examiner—Donald G. Daus
Assistant Examiner—Mary Vaughn
Attorney, Agent, or Firm—Bacon & Thomas

[57] ABSTRACT

Glycyrrhetinic acid esters of the formula:

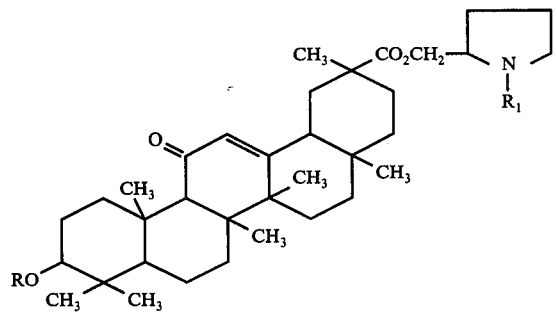

wherein R is hydrogen or an acyl radical of 2 to 20 carbon atoms and $R_1$ is a lower alkyl of 1 to 4 carbon atoms and the haloacid or alkylsulfate quaternary ammonium salts thereof as well as a process for preparing same are provided. The compounds of the invention display anti-inflammatory, antihistaminic, and anti-ulcer pharmacological activity.

11 Claims, No Drawings

TRITERPENE DERIVATIVES

BACKGROUND OF THE INVENTION

The present invention relates to new products of pharmacological interest and, more specifically, to new derivatives of glycyrrhetinic acid characterized by their pharmacological effect as inhibitors of gastroduodenal ulcers.

Glycyrrhetinic acid is prepared from glycyrrhizic acid which in turn is isolated from licorice root. Glycyrrhiza, as well as glycyrrhizic acid, in various extract and purified forms have long been utilized in pharmaceutical preparations as sweetening and flavoring agents. Glycyrrhetinic acid has also been heretofore utilized to a limited extent as an antiinflammatory and in the treatment of gastroduodenal ulcers.

SUMMARY OF THE INVENTION

It is a primary object of the present invention, therefore, to provide new ester derivatives of glycyrrhetinic acid and haloacids and alkyl sulfate quaternary salts of the prepared esters.

Another object of this invention is to provide a simple and efficient process for preparing glycyrrhetinic acid esters and quaternary salts thereof.

A further object of the instant invention is to provide glycyrrhetinic acid derivatives evidencing valuable therapeutic effectiveness especially in the prevention and management of gastroduodenal ulcers and which also display anti-inflammatory, antihistaminic and neurotropic and musculotropic activity.

DETAILED DESCRIPTION

Accordingly, the present invention provides basic esters of glycyrrhetinic acid represented by general formula I:

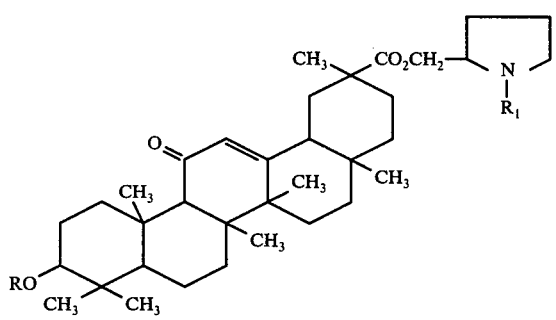

in which R is hydrogen or an acyl radical of 2 to 20 carbon atoms, for example, acetyl, palmitoyl, stearoyl and $R_1$ is a lower alkyl group, preferably, methyl.

The present invention also includes the corresponding quaternary ammonium derivatives of the basic esters of glycyrrhetinic acid represented by general formula II:

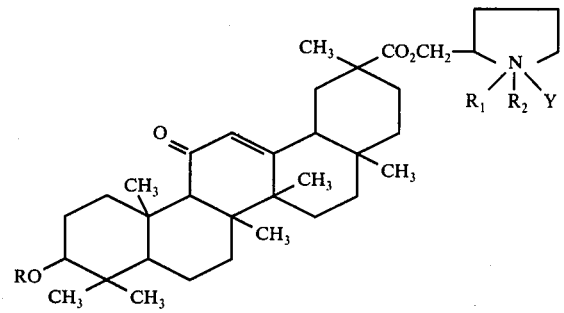

where R and $R_1$ have the same meaning as defined above; $R_2$ is a lower alkyl of 1 to 4 carbon atoms; and Y is a halogen radical or an alkylsulfate.

The present invention also provides a process for the preparation of the compounds of formula I wherein a 1-alkyl-2-halomethylpyrrolidine of the general formula

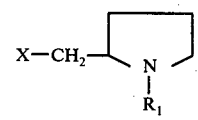

where X is chlorine or bromine, reacts with a glycyrrhetinic acid or derivative of the general formula IV:

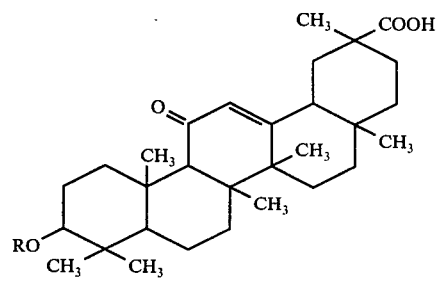

where R is the same as above to yield the compounds of the general formula 1 as chlorhydrate or bromhydrate.

These salts are then converted to the free base by treatment with alkali in aqueous or alcoholic media.

The reaction process is carried out in an appropriate solvent at under suitable temperature conditions. Generally the reactants are mixed in equimolar quantities or substantially equimolar quantities in an appropriate solvent, such as isopropyl alcohol, and the resulting mixture is boiled under reflux. It is not necessary to stir the mixture, although this may be advantageous under some circumstances. Reaction time is dependent on specific conditions but is usually on the order of 12 hours.

The reaction solvents are not critical and any solvent in which the reactants are soluble or substantially soluble and which allow the desired reaction product to be easily separated and recovered may be utilized in accordance with the present invention. For example, water, lower alcohols, especially, isopropanol, dioxane, halogenated hydrocarbons, such as chloroform, heterocyclic nitrogen compounds such as pyridine carboxylic acids and esters and the like as well as mixtures thereof may be employed as reaction solvents.

The temperature at which the reactions either the esterification or quaternization, are carried out, of course, depends on the particular reactants and solvents selected, but generally the temperature ranges between 25° C. and boiling under reflux conditions of the reaction mixture.

The most favorable results are obtained when the process is applied to obtain a product of formula V:

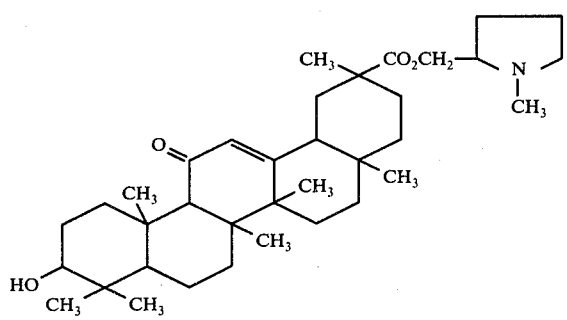

The preferred solvent for the preceding reaction has been found to be isopropyl alcohol since upon cooling the final mixture, the product crystallizes and can be separated easily by filtration, washed with appropriate solvents and finally dried.

The compounds obtained, as described previously and represented by general formula 1, can be used as intermediates in the preparation of the corresponding quaternary ammonium compounds represented by general formula II.

The present invention, therefore, also includes a process for the preparation of the quaternary ammonium compounds in which a compound of general formula 1 prepared as previously described, reacts with an alkyl ester or halide of the general formula $R_2Y$ to yield the compounds represented by general formula II.

The preferred esters for this aspect of the process are methylsulfate, methyliodide and methylbromide. In any case, the anion Y may be replaced by any conventional anion where it is desirable from a pharmaceutical or chemical standpoint using any known process for this type of replacement; for instance, treatment of the product of the general formula II with the silver salt of the anion which is to be introduced in the molecule.

The formation of the quaternary ammonium salt is carried out generally in an inert solvent with respect to the compounds of general formula I, such as benzene, methylisobutylacetone or butanone. The process can be carried out at room temperature or at elevated temperature and the time of the reaction generally depends on the temperature selected. Normally, the quaternary ammonium salt precipitates in the reaction medium from which it is filtered, washed and dried.

The described process pertains also to optically active or inactive 1-alkyl-2-halomethylpyrrolidine as well as the different isomeric forms of glycyrrhetinic acid and to their mixtures.

The invention is further illustrated by the following non-limiting examples:

EXAMPLE 1

2-(glycyrrhetinoyl methyl)N-methylpyrrolidine hydrochloride 40 parts of glycyrrhetinic acid, 10 parts 2-chloromethyl-N-methylpyrrolidine and 500 parts isopropylalcohol are mixed, then heated under reflux and stirring for 72 hours.

The solid product is filtered and washed with warm isopropyl alcohol and dried in an oven. The yield is 30 to 40 parts of the product as a white, crystalline, solid which melts with decomposition at 280° C. (s.c.).

Thin layer chromatography on silica gel eluted with benzene/methanol/acetic acid 7:3:1 shows a $R_F$ of 0.45 and eluted with benzene/acetone acetic acid 7:3:1 the $R_F$ is 0.05.

This solid treated with an alkali solution in diethyleneglycol at 100° C. for 3 to 5 minutes, regenerates glycyrrhetinic acid unaltered as shown by thin layer chromatography.

EXAMPLE 2

2-(glycyrrhetinoylmethyl)-N-methylpyrrolidine base 10 parts 2(glycyrretinoyl methyl) N-methyl pyrrolidine hydrochloride obtained as in Example 1 are dissolved in 300 parts of a mixture of water and alcohol (3-1). To this solution was added a slightly stoichimetric excess of aqueous sodium hydroxide. The product was extracted thrice with 50 parts of chloroform. The different chloroform extracts are washed with water, then dried over anhydrous sodium sulphate and finally evaporated until dry. The solid residue is crystallized from alcohol-water using active carbon as the decolorizing agent. The desired product 2(glycyrrhetinoyl methyl) N-methylpyrrolidine base is obtained as a white amorphous solid of m.p. 123° – 125° C. (s.c.). Yield is 85–90%.

EXAMPLE 3

2-(glycyrrhetinoyl methyl) N-methyl pyrrolidine methylsulfate

2(glycyrrhetinoyl methyl) N-methyl pyrrolidine base was dissolved in 50 parts methyl isobutylacetone, and 1.2 parts methylsulfate added. The resulting mixture is stirred for 30 minutes at room temperature and for 30 minutes more under reflux. The reaction mixture is cooled, filtered, washed with 10 parts methylisobutylacetone and with 10 parts n-hexane and the solid obtained is dried in the oven.

The product yield is 70–80% as a white or slightly colored solid with m.p. 271°–275° C. This product can be crystallized from alcohol-water solutions.

EXAMPLE 4

2(glycyrrhetinoyl methyl) N-methylpyrrolidine methylbromide 6 parts of 2-(glycyrrhetinoyl) N-methylpyrrolidine, 2 parts methylbromide and 50 parts benzene are refluxed 6 hours with an efficient reflux condenser. The mixture is cooled, the solid is filtered, washed with benzene and n-hexane and then dried. The product, 2(glycyrrhetinoyl N-methyl-pyrrolidine) methylbromide has a m.p. of 250° C. and the yield is 80%.

This product, as well as the one of Example 3, demonstrates outstanding activity as neurotropic, nusculotropic antihistaminic, anti-ulcer and healing agents in different artificially invoked conditions in mice, rats, Guinea pigs, rabbits and dogs and consequently are considered as potentially therapeutic agents. The anti-ulcer action of these compounds is demonstrated in the following Table wherein ulcers were artificially invoked utilizing various ulcerogenic techniques or agents in host rats.

TABLE 1

Anti-Ulcer Action of
2-(glycyrrhetinoyl methyl) N-methyl pyrrolidine methylsulfate
and
2-(glycyrrhetinoyl methyl) N-methyl pyrrolidine methylbromide

| Ulcerogenic Agent or Method | Dose mg./Kg. (Anti-Ulcer Agent) | Administration Route | Inhibition % Compound of Example 3 | Inhibition % Compound of Example 4 |
| --- | --- | --- | --- | --- |
| Reserpine | 5 | Intra-peritoneal | 42 | 8 |
|  | 10 | " | 25 | 47 |
|  | 25 | " | 25 | 13 |
| Psychosomatic | 5 | Oral | 42 | 52 |
| Frustration | 10 | " | 33 | 43 |
| (M. Bonfils) | 20 | " | 18 | — |
|  | 50 | " | — | 25 |
| Pyloric Ligature | 2.5 | Intra-peritoneal | 52 | — |
| (M. Shay) | 5 | " | — | 65 |
|  | 10 | " | 69 | 55 |
|  | 15 | " | 48 | — |
|  | 25 | " | 69 | — |
|  | 5 | Intra-dermal | 36 | 29 |
|  | 10 | " | — | 24 |
|  | 2.5 | " | — | 27 |
| Phenylbutazone | 5 | Oral | — | 22 |
|  | 10 | " | — | 23 |

EXAMPLE 5

2(glycyrrhetinoyl methyl) N-methylpyrrolidine methyliodide 10 parts of 2(glycyrrhetinoyl) N-methyl pyrrolidine, 3 parts methyl iodide and 100 parts toluene are refluxed for 6 hours. The solid product is separated by filtration, washed and dried. There are obtained 6 to 10 parts of the product, 2(glycyrrhetinoyl) N-methylpyrrolidine methoiodide m.p. 247°–250° C.

EXAMPLE 6

2(glycyrrhetinoyl methyl) N-methylpyrrolidine ethylbromide

As in Example 5 but using ethyl iodide instead of methylbromide. The product is obtained in a yield of 20 to 30% m.p. 224°–226°.

EXAMPLE 7

2(acetylglycyrrhetinoyl methyl) N-methylpyrrolidine Hel

As in Example 1, using the acetyl derivative instead of glycyrrhetinic acid. Yield 20–25 parts.

EXAMPLE 8

2(acetyl glycyrrhetinoyl methyl) N-methylpyrrolidine base

As in Example 2, using 2(acetylglycyrrhetinoyl methyl)N-methylpyrrolidine hydrochloride.

EXAMPLE 9

2(acetylglycyrrhetinoyl methyl) N-methylpyrrolidine methylsulfate

As in Example 3, with methylsulfate. The product has a melting point of 220° C.

What is claimed is:

1. Compounds of the formula

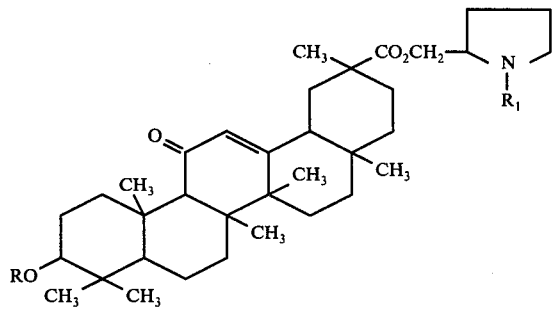

wherein R is hydrogen or a carboxylic acyl group of 2 to 20 carbon atoms and $R_1$ is a lower alkyl group.

2. Compounds of the formula

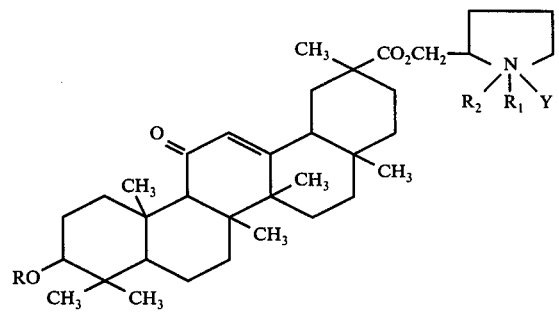

wherein R is hydrogen or a carboxylic acyl group of 2 to 20 carbon atoms, $R_1$ and $R_2$ are lower alkyl of 1 to 4 carbon atoms and Y is a pharmaceutically acceptable anion.

3. The compound of claim 1 having the formula

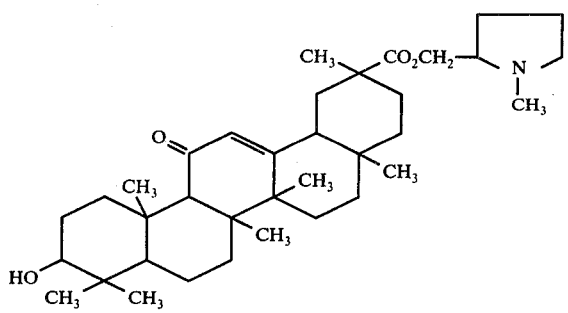

4. The compound of claim 2 consisting of 2(glycyrrhetinoylmethyl)N-methylpyrrolidine methylsulfate.

5. The compound of claim 2 consisting of 2(glycyrrhetinoylmethyl)N-methylpyrrolidine methylbromide.

6. A process for treating gastroduodenal ulcers comprising administering a therapeutically effective amount of the compound defined by claim 1.

7. A process for treating gastroduodenal ulcers comprising administering a therapeutically effective amount of the compound defined by claim 2.

8. The process as defined by claim 6, wherein the amount of compound administered is between about 2 and 50 mg./Kg.

9. The process as defined by claim 6, wherein the amount of compound administered is between about 5 and 25 mg./Kg.

10. The process as defined by claim 7, wherein the amount of compound administered is between about 2 and 50 mg./Kg.

11. The process as defined by claim 7, wherein the amount of compound administered is between about 5 and 25 mg./Kg.

* * * * *